United States Patent
Kato et al.

(10) Patent No.: US 10,352,827 B2
(45) Date of Patent: Jul. 16, 2019

(54) TIRE CONTACT STATE ESTIMATION METHOD

(71) Applicant: BRIDGESTONE CORPORATION, Chuo-ku, Tokyo (JP)

(72) Inventors: Hiroshi Kato, Hachioji (JP); Takahisa Kamikura, Machida (JP); Ryo Sakurai, Kokubunji (JP); Yasushi Hanatsuka, Nishitokyo (JP); Yasumichi Wakao, Musashino (JP)

(73) Assignee: BRIDGESTONE CORPORATION, Chuo-ku, Tokyo (JP)

( * ) Notice: Subject to any disclaimer, the term of this patent is extended or adjusted under 35 U.S.C. 154(b) by 185 days.

(21) Appl. No.: 14/889,931

(22) PCT Filed: May 12, 2014

(86) PCT No.: PCT/JP2014/002491
§ 371 (c)(1),
(2) Date: Nov. 9, 2015

(87) PCT Pub. No.: WO2014/199557
PCT Pub. Date: Dec. 18, 2014

(65) Prior Publication Data
US 2016/0109331 A1 Apr. 21, 2016

(30) Foreign Application Priority Data
Jun. 12, 2013 (JP) .................................. 2013-124029

(51) Int. Cl.
*G01M 17/02* (2006.01)
*B60C 23/04* (2006.01)
(Continued)

(52) U.S. Cl.
CPC ........... *G01M 17/02* (2013.01); *B60C 11/246* (2013.01); *B60C 23/04* (2013.01); *B60C 23/061* (2013.01);
(Continued)

(58) Field of Classification Search
CPC ..... B60C 11/246; B60C 23/04; B60C 23/061; B60W 40/00
(Continued)

(56) References Cited

U.S. PATENT DOCUMENTS 7,203,579 B2 * 4/2007 Yokota et al. ...... B60C 23/0477
303/150
2003/0156023 A1 8/2003 Kawasaki et al.

FOREIGN PATENT DOCUMENTS

| CN | 1852814 A | 10/2006 |
|---|---|---|
| EP | 1479580 A1 | 11/2004 |

(Continued)

OTHER PUBLICATIONS

English translation and bibliographic data of JPH07108842A, Title: Controller of Torque Transfer Between Right/Left Wheels for Vehicle, Date: Apr. 25, 1995, Publisher: European Patent Office, Espacenet; pp. total: 73.*
(Continued)

*Primary Examiner* — Jonathan M Dunlap
(74) *Attorney, Agent, or Firm* — Kenja IP Law PC

(57) ABSTRACT

A tire contact state estimation method includes: an information acquisition step of acquiring information of the tire; a correlation strength calculation step of calculating a first correlation strength between the rotational velocity and the braking and driving force, and also calculating a second correlation strength between the slip angle and the generated lateral force; a change detection step of detecting whether the first correlation strength has increased or decreased by a
(Continued)

Correlation strength relation diagram

| | Rotational velocity ⇔ Braking and driving force | Slip angle ⇔ Generated lateral force |
|---|---|---|
| Low-friction road | Strong | Weak |
| Decrease in internal pressure | Weak | Weak |
| Progress of abrasion | Weak | Strong | first threshold or more with respect to a predetermined first reference value, and also detecting whether the second correlation strength has increased or decreased by a second threshold or more with respect to a predetermined second reference value; and an estimation step of estimating at least two of the following: a condition of a road surface in contact with the tire, a tire internal pressure state, and a tire abrasion state.

12 Claims, 2 Drawing Sheets

(51) Int. Cl.
*B60T 8/172* (2006.01)
*B60W 40/068* (2012.01)
*G01L 17/00* (2006.01)
*B60C 23/06* (2006.01)
*B60C 11/24* (2006.01)
*G01N 3/56* (2006.01)

(52) U.S. Cl.
CPC ........... *B60T 8/172* (2013.01); *B60W 40/068* (2013.01); *G01L 17/00* (2013.01); *G01N 3/56* (2013.01); *B60T 2210/12* (2013.01); *B60T 2230/02* (2013.01)

(58) Field of Classification Search
USPC ......................................... 73/8, 146; D10/86
See application file for complete search history.

(56) References Cited

FOREIGN PATENT DOCUMENTS

| | | | |
|---|---|---|---|
| JP | 07108842 A | * | 4/1995 |
| JP | 2003-211925 A | | 7/2003 |
| JP | 2004-345521 A | | 12/2004 |
| JP | 2006-138668 A | | 6/2006 |
| JP | 2010-195325 A | | 9/2010 |
| JP | 2012-153290 A | | 8/2012 |
| WO | 2005/016670 A1 | | 2/2005 |

OTHER PUBLICATIONS

Jul. 15, 2014, International Search Report issued in International Patent Application No. PCT/JP2014/002491, 2 pages.

* cited by examiner

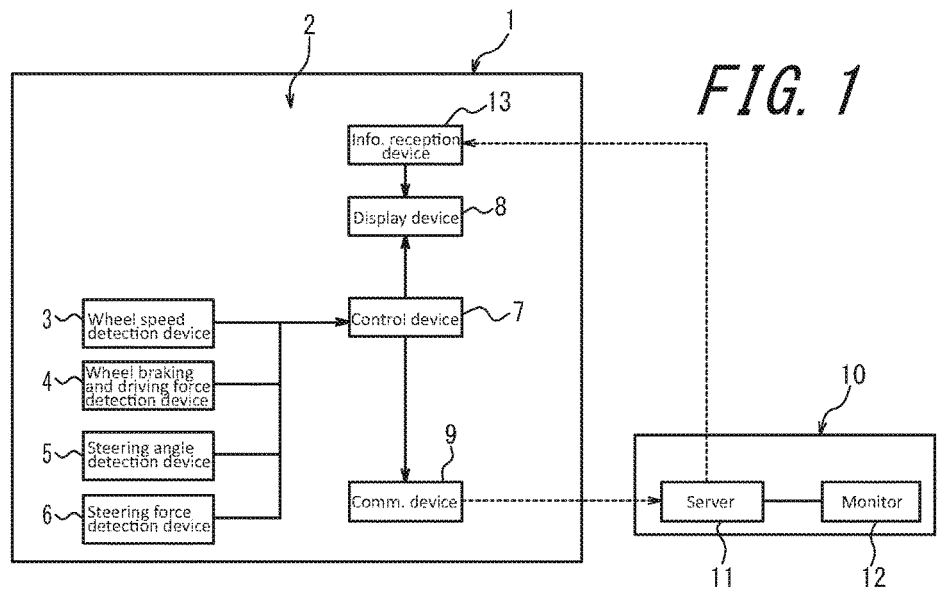
FIG. 1
FIG. 2 Correlation strength relation diagram
|  | Rotational velocity ⇔ Braking and driving force | Slip angle ⇔ Generated lateral force |
|---|---|---|
| Low-friction road | Strong | Weak |
| Decrease in internal pressure | Weak | Weak |
| Progress of abrasion | Weak | Strong |
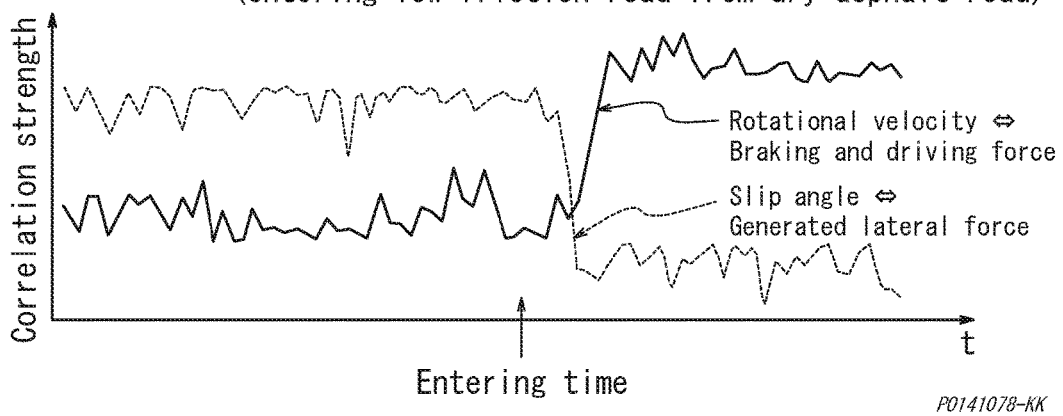
FIG. 3 Temporal change in correlation strength (entering low-friction road from dry-asphalt road)

TIRE CONTACT STATE ESTIMATION METHOD

TECHNICAL FIELD

This disclosure relates to a tire contact state estimation method of estimating information on a contact state of a tire mounted on a vehicle to a road surface.

BACKGROUND

In order to ensure driving safety of a vehicle such as an automobile, information on a contact state of a tire mounted on the vehicle to a road surface is understood.

For example, PLT 1 set forth below describes a technique to detect a vehicle speed and a steering angle of the vehicle during traveling and, based on detected values, estimate a friction coefficient of the road surface in contact with the tire.

CITATION LIST

Patent Literature

PLT 1: JP-A-2012-153290

SUMMARY

Technical Problem

However, the method disclosed in the PLT 1 calculates a front wheel SAT (self-aligning torque) estimated value and the like based on estimated values of the vehicle speed, the steering angle, and the friction coefficient of the road surface, and detects actual values thereof, and then estimates the friction coefficient of the road surface as a value corrected based on an error of the estimated values from the actual values. Therefore, there has been a problem to complicate a system for acquiring information on the contact state of the tire to the road surface necessary for the driving safety.

In order to solve the problem of the conventional technique as described above, it could be helpful to provide a tire contact state estimation method capable of, without using a complicated system, estimating a plurality of information on a tire contact state.

Solution to Problem

A tire contact state estimation method of the disclosure herein includes:

an information acquisition step of acquiring information on a rotational velocity, information on braking and driving force, information on a slip angle, and information on generated lateral force of the tire;

a correlation strength calculation step of calculating a first correlation strength between the rotational velocity and the braking and driving force from the information on the rotational velocity and the information on the braking and driving force those acquired at the information acquisition step, and also calculating a second correlation strength between the slip angle and the generated lateral force from the information on the slip angle and the information on the generated lateral force those acquired at the information acquisition step;

a change detection step of detecting whether the first correlation strength calculated at the correlation strength calculation step has increased or decreased by a first threshold or more with respect to a predetermined first reference value, and also detecting whether the second correlation strength calculated at the correlation strength calculation step has increased or decreased by a second threshold or more with respect to a predetermined second reference value; and an estimation step of estimating, based on a result of the detection at the change detection step, at least two of the following: a condition of the road surface in contact with the tire, a tire internal pressure state, and a tire abrasion state.

Thereby, based on the correlation strength of the information on the rotational velocity, the braking and driving force, the slip angle, and the generated lateral force of the tire, at least two of the following: the condition of the road surface in contact with the tire, the tire internal pressure state, and the tire abrasion state may be estimated. Therefore, a plurality of information on the contact state of the tire to the road surface that are necessary for driving safety may be easily estimated without using a complicated system.

The tire contact state estimation method of the disclosure herein, preferably, at the change detection step, detecting whether a mean value of the first correlation strength for a predetermined period has increased or decreased by the first threshold or more with respect to the predetermined first reference value and also whether a mean value of the second correlation strength for the predetermined period has increased or decreased by the second threshold or more with respect to the predetermined second reference value. Also preferably, the predetermined period associated with a result of the detection at the change detection step used to estimate the tire internal pressure state at the estimation step is longer than the predetermined period associated with a result of the detection at the change detection step used to estimate the condition of the road surface in contact with the tire at the estimation step.

Thereby, the change in the correlation strength due to the change in a road surface condition and the change in the correlation strength due to the change in the tire internal pressure state may be accurately discriminated from each other in consideration of a time axis. Therefore, estimation accuracy of the information on the contact state of the tire to the road surface by the tire contact state estimation method may be improved.

The tire contact state estimation method of the disclosure herein, preferably, at the change detection step, detecting whether a mean value of the first correlation strength for a predetermined period has increased or decreased by the first threshold or more with respect to the predetermined first reference value and also whether a mean value of the second correlation strength for the predetermined period has increased or decreased by the second threshold or more with respect to the predetermined second reference value. Also preferably, the predetermined period associated with a result of the detection at the change detection step used to estimate the tire abrasion state at the estimation step is longer than the predetermined period associated with a result of the detection at the change detection step used to estimate the condition of the road surface in contact with the tire and the tire internal pressure state at the estimation step.

Thereby, the change in the correlation strength due to the change in the tire internal pressure state and the change in the correlation strength due to the change in the tire abrasion state may be accurately discriminated from each other in consideration of the time axis. Therefore, the estimation accuracy of the information on the contact state of the tire to the road surface by the tire contact state estimation method may be improved.

Advantageous Effect

The tire contact state estimation method capable of, without using a complicated system, estimating a plurality of information on a tire contact state may be provided.

BRIEF DESCRIPTION OF THE DRAWINGS

In the accompanying drawings:

FIG. 1 is a schematic block diagram of a tire state estimation system for implementing a tire contact state estimation method according to one embodiment;

FIG. 2 is a diagram illustrating a correspondence relation between correlation strength of information acquired by the tire state estimation system illustrated in FIG. 1 and information on a tire contact state;

FIG. 3 is a characteristic diagram illustrating an example of a temporal change in the correlation strength at the time of entering a low-friction road from a dry-asphalt road;

DETAILED DESCRIPTION

Figure 4:
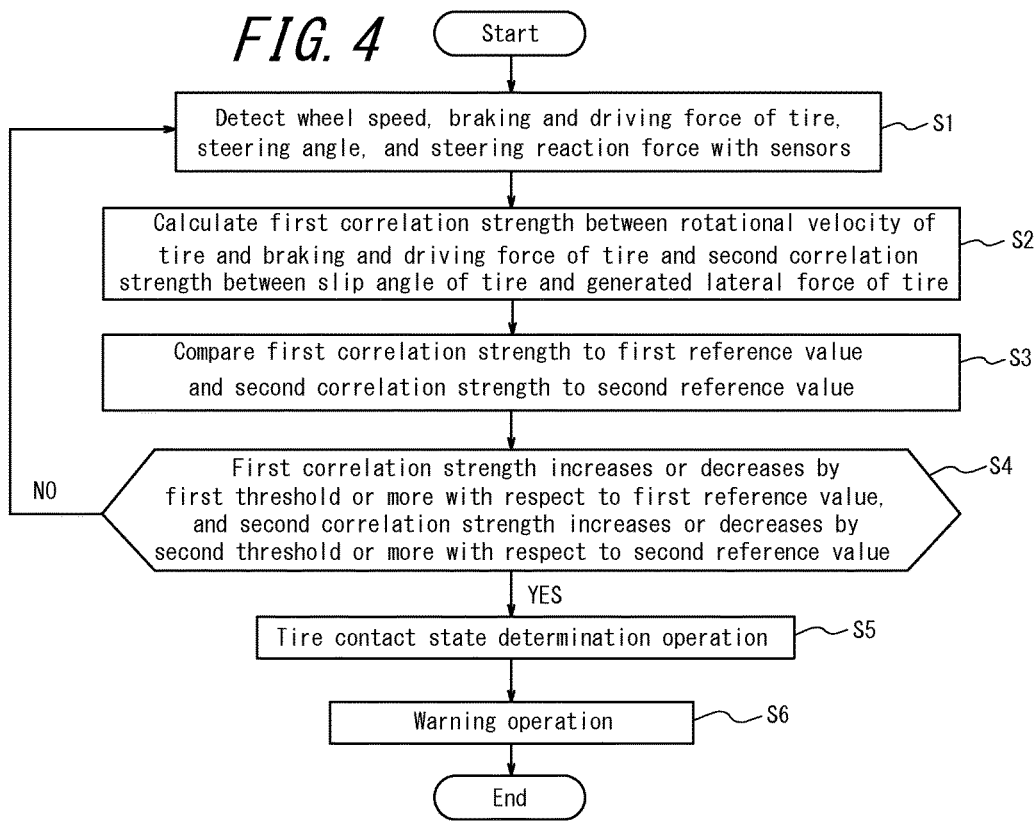
FIG. 4 is a flowchart of the tire contact state estimation method according to one embodiment.

Hereinafter, an embodiment of the disclosure herein will be described with reference to the accompanying drawings.

A tire contact state estimation method according to one embodiment estimates, as information on a contact state of a tire mounted on a vehicle (for example, an automobile) to a road surface, a condition of the road surface in contact with the tire, a tire internal pressure state, and a tire abrasion state. For example, the tire contact state estimation method estimates, as the condition of the road surface in contact with the tire, whether the road surface is a dry-asphalt road surface or a low-friction road surface such as a frozen road surface, a snow-covered road surface and the like. The tire contact state estimation method estimates, as the tire internal pressure state, whether a tire internal pressure has decreased within or over a permissible range or over from a normal value and also estimates, as the tire abrasion state, whether a tread surface of the tire has been worn out by a permissible quantity or more from a brand-new state. When at least one of the following is estimated: the road surface in contact with the tire is the low-friction road surface, the tire internal pressure has decreased within or over the permissible range or over from the normal value, and the tire has been worn out by the permissible quantity or more from the brand-new state, it may be detected that the contact state of the tire to the road surface is abnormal.

The tire contact state estimation method, as long as when the vehicle having a plurality of tires mounted thereon may change a traveling direction by steering the tire, is applicable to a variety of types of the vehicle such as, for example, a vehicle using an engine (an internal combustion engine) as a driving source, a vehicle using an electric motor as the driving source, and a vehicle using both the engine and the electric motor as the driving source.

The tire contact state estimation method, as illustrated in FIG. 1, for example, may be substantialized by using a tire state estimation system 2 mounted on a vehicle 1. The tire state estimation system 2 includes a wheel speed detection device 3, a wheel braking and driving force detection device 4, a steering angle detection device 5, and a steering force detection device 6.

The wheel speed detection device 3 detects a wheel speed, i.e., a rotational velocity of the tire (not illustrated) mounted on the vehicle 1 and outputs detection data to a control device 7. The wheel speed detection device 3 may be constituted by using, for example, a rotation sensor attached to a hub of each wheel for an anti-lock braking system. Note that the wheel speed detection device 3 is not limited to the rotation sensor for the anti-lock braking system as described above but may take any other configuration as long as capable of detecting a rotation of the tire.

The wheel braking and driving force detection device 4 detects braking force and driving force those applied to the tire and outputs detection data to the control device 7. Here, the braking force acting in a direction for reducing the rotational velocity of the tire and the driving force acting in a direction for increasing the rotational velocity of the tire are collectively referred to as braking and driving force.

When the vehicle 1 is an electric vehicle having the electric motor as the driving source, the wheel braking and driving force detection device 4 detects, for example, total driving force generated by the electric motor from power consumption thereof and distributes the total driving force to each tire at a ratio corresponding to the rotational velocity of each tire, thereby calculates the driving force of the tire. In this case, the braking force of the tire may be acquired by, when the vehicle 1 is decelerating with regenerative braking of the electric motor alone, detecting total braking force generated by the electric motor from electric power generation thereof and distributing the total braking force to each tire at the ratio corresponding to the rotational velocity of each tire. Information on the power consumption and the electric power generation of the electric motor may be acquired from a motor control device.

When the vehicle 1 is not the electric vehicle, or when the vehicle 1 is the electric vehicle that applies the brakes by using a braking means other than the regenerative brake, the wheel braking and driving force detection device 4 may estimate the braking and driving force of the tire from, for example, a behavior of the vehicle 1 during travelling. In this case, the braking and driving force of the tire may be calculated by using a vehicle model from preliminarily weighted weight, a vehicle yaw rate, longitudinal acceleration, lateral acceleration and the like, or by extracting a corresponding value of the braking and driving force preliminarily mapped in association with the vehicle behavior.

The steering angle detection device 5 detects a steering angle when the tire is steered and outputs the steering angle as information on a slip angle to the control device 7. Generally, the slip angle increases in proportion to the steering angle of the tire. Therefore, the steering angle may be used as information on the steering angle, i.e., a physical quantity that varies in response to a change in the slip angle. The steering angle detection device 5 may be constituted by using, for example, an angle sensor that is provided to a steering column or the like for a power steering device and detects a steering rotational angle. Note that the steering angle detection device 5 is not limited to the angle sensor for the power steering device as described above but may be constituted by using a different sensor or may take a configuration to detect a travelling direction of the vehicle 1 by using an optical sensor or the like mounted on the vehicle 1 and directly detect the slip angle from a result of the detection and the steering angle of the tire.

The steering force detection device 6 detects steering force necessary to steer the tire, i.e., steering reaction force generated upon steering the tire and outputs the steering reaction force to the control device 7. Generally, the generated lateral force of the tire increases in proportion to the steering reaction force of the tire. Therefore, the steering reaction force may be used as information on the generated lateral force of the tire, i.e., a physical quantity that varies in response to a change in the generated lateral force. The steering force detection device 6 may be constituted by using, for example, a torque sensor provided to the steering column or the like for the power steering device. Note that the steering force detection device 6 is not limited to the torque sensor for the power steering device as described above but may take any configuration as long as capable of detecting the steering reaction force and the generated lateral force of the tire. The generated lateral force of the tire refers to force in a lateral direction (a direction opposite to a centrifugal force) generated in the tire against the centrifugal force when the vehicle is turning.

The control device 7 for receiving the inputs of the detection values (the detection data) from each of the detection devices 3 to 6 functions as, for example, an arithmetic processing device (a microcomputer) equipped with a CPU, a memory and the like. The control device 7 may be constituted by using, for example, a vehicle-mounted computer such as ECU (Engine Control Unit) mounted on the vehicle 1. In this case, each of the detection devices 3 to 6 may be connected to the control device 7 via in-vehicle network (in-vehicle LAN) such as CAN or the like provided to the vehicle 1.

As described above, the control device 7 acquires the information on the rotational velocity of the tire from the input of the wheel speed detection device 3, the information on the braking and driving force of the tire from the input of the wheel braking and driving force detection device 4, the information on the slip angle (the information on the steering angle) of the tire from the input of the steering angle detection device 5, and the information on the generated lateral force (information on the steering reaction force) of the tire from the input of the steering force detection device 6 (an information acquisition step). Note that those information acquired by the control device 7 may be either values detected by the detection devices 3 to 6 or values calculated from the detected values, as long as including values corresponding to desired information.

The control device 7, from the information on the rotational velocity (the wheel speed) of the tire and the information on the braking and driving force of the tire those being acquired, may calculate correlation strength between the rotational velocity and the braking and driving force as first correlation strength (correlation strength calculation step). Also, the control device 7, from the information on the slip angle (the steering angle) and the information on the generated lateral force of the tire (the steering reaction force) those being acquired, may calculate second correlation strength between the slip angle of the tire and the generated lateral force of the tire (the correlation strength calculation step). In this embodiment, that is, the control device 7 calculates the second correlation strength between the slip angle and the generated lateral force of the tire from the steering angle and the steering reaction force of the tire.

Note that the correlation strength described above functions as an index indicative of strength of a correlation between the two acquired values (the detected values) and corresponds to a correlation coefficient. The correlation strength, at the correlation strength calculation step described above, may be calculated by using a statistical processing technique commonly referred to as pattern recognition such as, for example, an independent component analytical method.

The control device 7 may detect whether the first correlation strength calculated has increased or decreased by a first threshold or more with respect to a first reference value that is predetermined (a change detection step). Also, the control device 7 may detect whether the second correlation strength calculated has increased or decreased by a second threshold or more with respect to a second reference value that is predetermined (the change detection step). The first reference value, the second reference value, the first threshold, and the second threshold are calculated from, for example, a result of a driving test carried out with an appropriate tire contact state, and preliminarily stored in a storage means such as a memory of the control device 7. That is, on the dry-asphalt road surface (with a friction coefficient $\mu$ at approximately 1.0), the vehicle having new tires with a prescribed internal pressure mounted thereon is subjected to a running test, in which the rotational velocity, the braking and driving force, the steering angle, and the steering reaction force of the tire in an appropriate state are measured. Then, the correlation strength between the rotational velocity and the braking and driving force when the tire contact state calculated from the values measured in the running test is appropriate is regarded as the first reference value and stored in the storage means, and the correlation strength between the steering angle and the steering reaction force when the tire contact state is appropriate is regarded as the second reference value and stored in the storage means. Note that, in order to estimate the road surface condition, in place of the first reference value and the second reference value those preliminarily stored in the storage means by the method as described above, a mean value of the first correlation strength and a mean value of the second correlation strength those for a predetermined period from a current time calculated at the above correlation strength calculation step may be used as the first reference value and the second reference value, respectively.

On the other hand, the first threshold and the second threshold are appropriately determined based on the result of the running test carried out by changing the road surface condition, the tire internal pressure state, and the tire abrasion state. Preferably, these thresholds are set at values that, for example, allows determination that safe driving of the vehicle 1 cannot be maintained when the tire contact state is appropriate and each correlation strength becomes higher or lower than the values. Note that the first threshold and the second threshold may be set at a plurality of values each applicable to estimation of a change in the road surface condition, estimation of a change in the tire internal pressure, or estimation of the tire abrasion state. Or, the first threshold and the second threshold may be different between an increasing side and a decreasing side with respect to each of the reference values. Further, the first threshold and the second threshold are not limited to absolute values but may be, for example, the absolute values when estimating the change in the tire abrasion state, and a relative value having a predetermined range with respect to the mean values of the first correlation strength and the second correlation strength for the predetermined period and varying according to the change in the correlation strength when estimating the change in the road surface condition.

The control device 7, by applying the increase or decrease in the first correlation strength by the first threshold or more with respect to the first threshold and the increase or decrease in the second correlation strength by the second threshold or more with respect to the second reference value to a correlation pattern illustrated in FIG. 2, may estimate the condition of the road surface in contact with the tire, the tire internal pressure state, and the tire abrasion state (an estimation step). Note that, in FIG. 2, "strong" indicates strong correlation strength when the correlation strength increases by the threshold or more with respect to the reference value, and "weak" indicates weak correlation strength when the correlation strength decreases by the threshold or more with respect to the reference value.

When the road surface on which the vehicle 1 is traveling is the low-friction road surface with a friction coefficient lower than that of an appropriate road surface condition, i.e., the dry-asphalt road surface (with the μ at approximately 1.0), since the friction against the low-friction road is small with respect to the change in the braking and driving force, the change in the rotational velocity of the tire increases more than that in the appropriate road surface condition. On the other hand, since the reaction force applied to the tire from the road surface when the slip angle changes is smaller than the reaction force applied to the tire in the appropriate road surface condition, a change in the generated lateral force of the tire in response to the change in the slip angle of the tire is smaller than that in the appropriate road surface condition. That is, as illustrated in FIG. 3, in viewing in terms of the correlation strength, when the condition of the road surface on which the vehicle 1 is traveling changes from the appropriate dry-asphalt road surface to the low-friction road surface, the correlation strength between the rotational velocity of the tire and the braking and driving force of the tire becomes strong, and the correlation strength between the slip angle of the tire and the generated lateral force of the tire becomes weak. Applying this pattern to the relation illustrated in FIG. 2, the control device 7, when detecting at the change detection step that the correlation strength between the rotational velocity of the tire and the braking and driving force of the tire becomes strong and also that the correlation strength between the slip angle of the tire and the generated lateral force of the tire becomes weak, may infer that the road surface condition has changed from the appropriate road surface to the low-friction road surface.

When the internal pressure of the tire mounted on the vehicle 1 becomes lower than a normal internal pressure, a spring constant of the tire becomes smaller than that in a normal state. Therefore, a response of the change in the rotational velocity of the tire to the change in the braking and driving force of the tire is delayed, and a response of the change in the generated lateral force of the tire to the change in the slip angle of the tire is also delayed. That is, in viewing in terms of the correlation strength, when the tire internal pressure becomes lower than the normal internal pressure, the first correlation strength between the rotational velocity of the tire and the braking and driving force of the tire and the second correlation strength between the slip angle of the tire and the generated lateral force of the tire both become weak. Applying this pattern to the relation illustrated in FIG. 2, the control device 7, when detecting at the change detection step that the correlation strength between the rotational velocity of the tire and the braking and driving force of the tire becomes weak and also that the correlation strength between the slip angle of the tire and the generated lateral force of the tire becomes weak, may infer that the tire internal pressure has decreased within or over the permissible range or over.

As abrasion of the tire progresses, generally, a groove area of a tread pattern on a tire surface is reduced, that is, a ratio of the groove area on the tire surface is reduced and an effective abrasion coefficient increases. Therefore, the reaction force of the road surface to the change in the rotational velocity of the tire increases, and a responsive amount of the rotational velocity of the tire with respect to the change in the braking and driving force of the tire decreases. On the other hand, the change in the generated lateral force of the tire with respect to the change in the slip angle of the tire increases. That is, in viewing in terms of the correlation strength, as the abrasion of the tire progresses further, the first correlation strength between the rotational velocity of the tire and the braking and driving force of the tire becomes weaker, and the second correlation strength between the slip angle of the tire and the generated lateral force of the tire becomes stronger. Applying such a pattern to the relation illustrated in FIG. 2, the control device 7, when detecting at the change detection step that the correlation strength between the rotational velocity of the tire and the braking and driving force of the tire becomes weak and also that the correlation strength between the slip angle of the tire and the generated lateral force of the tire becomes strong, may infer that the abrasion of the tire has progressed within or over a permissible range.

As illustrated in FIG. 1, the control device 7 is connected to a display device 8 such as a monitor or the like. Therefore, the control device 7, when detecting an abnormal contact state of the tire to the road surface, may display accordingly in the display device 8. When the abnormal contact state of the tire is detected, together with or separately from a warning displayed in the display device 8, an alarm may be generated from a speaker or the like provided in the vehicle 1. The display device 8 and the speaker may be constituted by using those used for a navigation system or the like preliminarily mounted on the vehicle 1.

Also, a system may be provided in which the control device 7 is connected to a communication device 9 such as a communication card or a mobile terminal and may transfer information on the warning to a server 11 installed in a management office 10 or the like outside the vehicle, such that the abnormal contact state of the tire generated in the vehicle 1 may be viewed on a monitor 12 (a web screen or the like) in the management office 10. Upon receiving notification of the abnormal contact state of the tire, the management office 10 may, for example, prepare for replacement of the tire of the vehicle 1. Also, the management office 10 may know a location where the road surface is slippery from the information on the warning and display the location on a map. Further, a system may be provided in which the management office 10 transmits information on the map indicating the location where the road surface is slippery to an information reception device 13 mounted on the vehicle 1 and other vehicles, such that the information on the map is shared among the vehicle 1 and other vehicles. The information reception device 13 may be constituted by using one that is used to receive traffic information and the like in the navigation system and the like.

The configurations described above enable the driver to drive while confirming that the state of the tire and the road surface condition are appropriate and also, when the road surface is in a hazardous condition, may notify the driver accordingly and also notify nearby vehicles of that there is the road surface in the hazardous condition. Thereby, the safe driving of the vehicle may be substantialized.

Each of the detected values for calculating the first correlation strength and the second correlation strength may be detected by using existing detection devices 3 to 6 and the like mounted on the vehicle 1. Also, the control device 7, the display device 8, and the information reception device 13 may be constituted by using devices those preliminarily mounted on the vehicle 1. Therefore, without the necessity for addition of new sensors and devices, the tire state estimation system 2 for implementing the tire contact state estimation method may be configured in a simple and inexpensive manner.

The following is a description of a procedure for the tire contact state estimation method according to one embodiment of the disclosure herein as described above with reference to a flowchart illustrated in FIG. 4.

At step S1, first, the detection devices (sensors) 3 to 6 mounted on the vehicle 1 detect the wheel speed (the rotational velocity of the tire), the braking and driving force of the tire, the steering angle, and the steering reaction force, respectively, and these detected values are input to the control device 7 (the information acquisition step). At step S2, next, from these detected values, the first correlation strength between the rotational velocity of the tire and the braking and driving force of the tire and the second correlation strength between the slip angle of the tire and the generated lateral force of the tire are calculated (the correlation strength calculation step). After the calculation of the first correlation strength and the second correlation strength, at step S3, the first correlation strength is compared to the first reference value, and the second correlation strength is compared to the second reference value. At step S4, it is determined whether the first correlation strength has increased or decreased by the first threshold or more with respect to the first reference value, and also whether the second correlation strength has increased or decreased by the second threshold or more with respect to the second reference value (the change detection step).

When it is determined at step S4 that the first correlation strength has increased or decreased by the first threshold or more with respect to the first reference value and, also, the second correlation strength has increased or decreased by the second threshold or more with respect to the second reference value, a tire contact state determination operation is carried out at step S5. From the pattern illustrated in FIG. 2, it is inferred that the condition of the road surface in contact with the tire has changed to the low-friction road surface, that the tire internal pressure has decreased within or over the permissible range from the normal value, and that the tire abrasion state has progressed to the permissible quantity or more from the brand-new state (the inferring step), and thus the abnormal tire contact state is detected. Note that, at step S4, when at least one of the first correlation strength and the second correlation strength has not increased or decreased by or more than the first threshold or the second threshold with respect to the first reference value or the second reference value, or when both the first correlation strength and the second correlation strength increase by or more than the first threshold and the second threshold, a routine returns to step S1.

When the abnormal contact state of the tire to the road surface is detected at step S4, the warning is displayed in the display device 8 at step S6, and a warning operation is carried out such as by transmitting the information on the abnormal contact state from the communication device 9 to the server 11.

Figure 5:
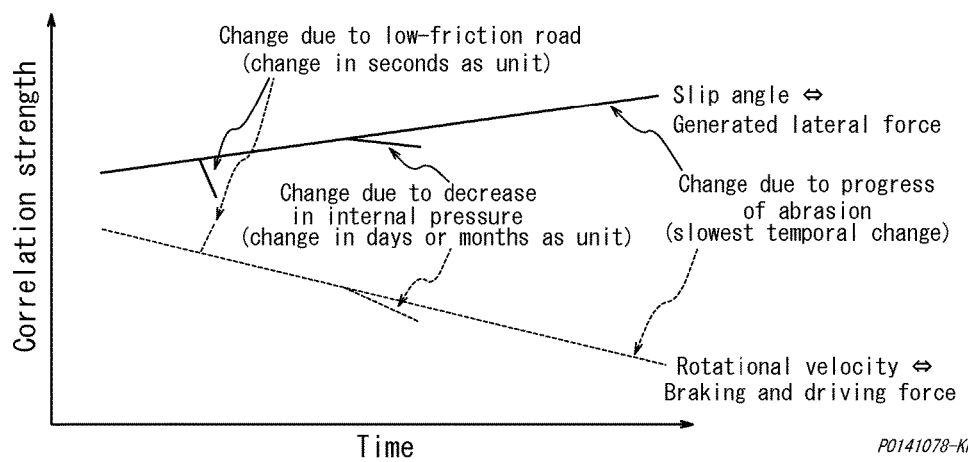
FIG. 5 is a diagram schematically illustrating a temporal change in each correlation strength.

FIG. 5 is a diagram schematically illustrating a temporal change in the correlation strength.

As illustrated in FIG. 5, the change in the road surface condition, the change in the tire internal pressure, and the change in the tire abrasion state have respective change rates significantly different from one another. Under a general use environment, the tire abrasion progresses at a changing rate in years as a unit, and the tire internal pressure changes at a changing rate in days or months as a unit. Also, the road surface condition such as, for example, slipperiness changes at a changing rate in seconds as a unit. Therefore, the tire contact state estimation method of the disclosure herein preferably utilizes a feature that the estimation subjects have temporal difference in the change rates and thereby further improves estimation accuracy by the following method.

That is, at the change detection step, the mean value of the first correlation strength for the predetermined period from the current time is calculated, and it is detected whether the mean value of the first correlation strength has increased or decreased by the first threshold or more with respect to the first reference value. At the change detection step, also, the mean value of the second correlation strength for the predetermined period from the current time is calculated, and it is detected whether the mean value of the second correlation strength has increased or decreased by the second threshold or more with respect to the second reference value. At the estimation step, in order to estimate the tire internal pressure state, the predetermined period used for the calculation of the mean value of each of the correlation strength is set longer than the predetermined period used for the estimation of the condition of the road surface in contact with the tire. Then, at the change detection step, the mean value calculated by using the predetermined period is used to detect the change in the tire internal pressure state. Similarly, in order to estimate the tire abrasion state, the predetermined period used for the calculation of the mean value of each of the correlation strength is set longer than the predetermined period used for the estimation of the tire internal pressure state. Then, at the change detection step, the mean value calculated by using the predetermined period is used to detect the tire abrasion state. As described above, as the first correlation strength and the second correlation strength, the mean values thereof for the predetermined period are used and, also, as the first correlation strength and the second correlation strength used for the estimation of the change in the road surface condition, the change in the tire internal pressure state, and the change in the tire abrasion state, the mean values for the predetermined periods with different lengths are used for the calculation. Thereby, the estimation accuracy of the tire contact state may be further improved.

For example, by using the mean values of the first correlation strength and the second correlation strength for a few seconds as the predetermined period, detection sensitivity for the change in the tire internal pressure state and the change in the tire abrasion state is lowered, and the change in the road surface condition alone may be accurately estimated. On the other hand, by using the mean values of the first correlation strength and the second correlation strength for the predetermined period in days or months as the unit, the detection sensitivity for the change in the road surface condition and the change in the tire abrasion state is lowered, and the change in the tire internal pressure state alone may be accurately estimated. Further, by using the mean values of the first correlation strength and the second correlation strength for the predetermined period in years as the unit (for example, one year), the information on the change in the road surface condition and the information on the change in the tire internal pressure are substantially eliminated, and the change in the tire abrasion state (an abrasion progression degree) alone may be accurately estimated.

EXAMPLES

Next, examples of the disclosure herein will be described.

An electric vehicle having an electric motor as a driving source was provided with a wheel speed detection device, a wheel braking and driving force detection device, a steering angle detection device, and a steering force detection device. In the examples, each of the devices is connected to a control device via the in-vehicle network (the in-vehicle LAN) such as the CAN or the like provided in the vehicle.

The driving force of the tire was calculated by detecting overall driving force from the power consumption of the electric motor and distributing the overall driving force to each tire at a ratio corresponding to a wheel speed of each tire.

In a running test, brand-new tires with the normal internal pressure were mounted on the vehicle described above and run on the dry-asphalt road (with the μ at approximately 1.0). Based on a result of the running test conducted in this manner, the first reference value, the second reference value, the first threshold, and the second threshold were determined. Note that the tires were of 195/65R17 in size with the internal pressure at 230 kPa. Also, in any of the running tests herein, the vehicle was driven on a straight line, and the steering was not fixed during the driving but maintained to drive on the straight line by minor steering.

When the tires in the above state were mounted on the vehicle and run on the low-friction road surface (with the μ at approximately 0.3), the tire contact state estimation method of the disclosure herein detected that, with respect to the appropriate tire contact state, the correlation between the rotational velocity of the tire and the braking and driving force of the tire, i.e., the first correlation strength became strong, and also that the correlation between the slip angle of the tire and the generated lateral force of the tire, i.e., the second correlation strength became weak. Thereby, it was inferred that the road surface condition was the low-friction road surface.

When the internal pressure of the above tire was changed to 170 kPa and the tires were run on the dry-asphalt road, the tire contact state estimation method of the disclosure herein detected that, with respect to the appropriate tire contact state, the correlation between the rotational velocity of the tire and the braking and driving force of the tire, i.e., the first correlation strength and the correlation between the slip angle of the tire and the generated lateral force of the tire, i.e., the second correlation strength both became weak. Thereby, it was inferred that the tire internal pressure had decreased.

When, in place of the above brand-new tires, tires (with the normal internal pressure) worn to a slip sign were mounted on the vehicle described above and run on the dry-asphalt road, the tire contact state estimation method of the disclosure herein detected that, with respect to the appropriate tire contact state, the correlation between the rotational velocity of the tire and the braking and driving force of the tire, i.e., the first correlation strength became weak and the correlation between the slip angle of the tire and the generated lateral force of the tire, i.e., the second correlation strength became strong. Thereby, it was inferred that the abrasion of the tire had progressed.

The disclosure herein is limited to neither the embodiment nor the examples described above but may be changed in various manners without departing from the gist thereof, as a matter of course. For example, although in the above embodiment the steering reaction force of the tire is used as the information on the generated lateral force of the tire, a self-aligning torque that varies in accordance with the steering of the tire similarly to the generated lateral force of the tire may be used as the information on the generated lateral force of the tire.

Further, although in the above embodiment, at the estimation step, the following three condition/states: the condition of the road surface in contact with the tire, the tire internal pressure state, and the tire abrasion state are estimated, at least two out of the three condition/states may be estimated.

1: vehicle, 2: tire state estimation system, 3: wheel speed detection device, 4: wheel braking and driving force detection device, 5: steering angle detection device, 6: steering force detection device, 7: control device

The invention claimed is:

1. A tire contact state estimation method of estimating information on a contact state of a tire mounted on a vehicle to a road surface, the tire contact state estimation method comprising:
   an information acquisition step of acquiring information, with a control device, on a rotational velocity from a wheel speed detection device, information on braking and driving force from a wheel braking and driving force detection device, information on a slip angle from a steering angle detection device, and information on generated lateral force of the tire from a steering force detection device;
   a correlation strength calculation step of calculating, by the control device, a first correlation strength between the rotational velocity and the braking and driving force from the information on the rotational velocity and the information on the braking and driving force those acquired at the information acquisition step, and also calculating, by the control device, a second correlation strength between the slip angle and the generated lateral force from the information on the slip angle and the information on the generated lateral force those acquired at the information acquisition step;
   a change detection step of detecting, by the control device, whether the first correlation strength calculated at the correlation strength calculation step has increased or decreased by a first threshold or more with respect to a predetermined first reference value, and also detecting, by the control device, whether the second correlation strength calculated at the correlation strength calculation step has increased or decreased by a second threshold or more with respect to a predetermined second reference value;
   an estimation step of estimating, by the control device based on a result of the detection at the change detection step, at least two of the following: a condition of the road surface in contact with the tire, a tire internal pressure state, and a tire abrasion state; and
   a display step of displaying a warning on a display device when an abnormal contact state of the tire to the road surface is detected at the change detection step;
   wherein the condition of the road surface in contact with the tire is estimated to have changed from an appropriate road surface to a low-friction road surface when the change detection step detects the first correlation strength having increased by the first threshold or more and the second correlation having decreased by the second threshold or more;
   the tire internal pressure state is estimated to have decreased when the change detection step detects the first correlation strength having decreased by the first threshold or more and the second correlation strength having decreased by the second threshold or more; and the tire abrasion state is estimated to have progressed when the change detection step detects the first correlation strength having decreased by the first threshold or more and the second correlation strength having increased by the second threshold or more.

2. The tire contact state estimation method according to claim 1, at the change detection step, detecting, by the control device, whether a mean value of the first correlation strength for a predetermined period has increased or decreased by the first threshold or more with respect to the predetermined first reference value and also detecting, by the control device, whether a mean value of the second correlation strength for the predetermined period has increased or decreased by the second threshold or more with respect to the predetermined second reference value, wherein the predetermined period associated with a result of the detection at the change detection step used to estimate the tire internal pressure state at the estimation step is longer than the predetermined period associated with a result of the detection at the change detection step used to estimate the condition of the road surface in contact with the tire at the estimation step.

3. The tire contact state estimation method according to claim 2, at the change detection step, detecting, by the control device, whether a mean value of the first correlation strength for a predetermined period has increased or decreased by the first threshold or more with respect to the predetermined first reference value and also detecting, by the control device, whether a mean value of the second correlation strength for the predetermined period has increased or decreased by the second threshold or more with respect to the predetermined second reference value, wherein the predetermined period associated with a result of the detection at the change detection step used to estimate the tire abrasion state at the estimation step is longer than the predetermined period associated with a result of the detection at the change detection step used to estimate the condition of the road surface in contact with the tire and the tire internal pressure state at the estimation step.

4. The tire contact state estimation method according to claim 1, at the change detection step, detecting, by the control device, whether a mean value of the first correlation strength for a predetermined period has increased or decreased by the first threshold or more with respect to the predetermined first reference value and also detecting, by the control device, whether a mean value of the second correlation strength for the predetermined period has increased or decreased by the second threshold or more with respect to the predetermined second reference value, wherein the predetermined period associated with a result of the detection at the change detection step used to estimate the tire abrasion state at the estimation step is longer than the predetermined period associated with a result of the detection at the change detection step used to estimate the condition of the road surface in contact with the tire and the tire internal pressure state at the estimation step.

5. A tire contact state estimation system of estimating information on a contact state of a tire mounted on a vehicle to a road surface, the tire contact state estimation system comprising:

a control device, a wheel speed detection device detecting a rotational velocity of the tire and outputting detection data to the control device, a wheel braking and driving force detection device detecting a braking and driving force of the tire and outputting detection data to the control device, a steering angle detection device detecting a slip angle of the tire and outputting detection data to the control device, a steering force detection device detecting a generated lateral force of the tire and outputting detection data to the control device, and a display device connected to the control device so that, when the control device detects an abnormal contact state of the tire to the road surface, the display device displays a warning, wherein the control device calculates a first correlation strength between the rotational velocity and the braking and driving force from the information on the rotational velocity of the tire from the input of the wheel speed detection device and the information on the braking and driving force of the tire from the input of the wheel braking and driving force detection device; and wherein the control device calculates a second correlation strength between the slip angle and the generated lateral force from the information on the slip angle of the tire from the input of the steering angle detection device, and the information on the generated lateral force of the tire from the input of the steering force detection device;

wherein the control device detects whether the first correlation strength calculated at the control device has increased or decreased by a first threshold or more with respect to a predetermined first reference value, and also detects whether the second correlation strength calculated at the control device has increased or decreased by a second threshold or more with respect to a predetermined second reference value;

wherein the control device estimates, based on a result of a detection at the control device, at least two of the following: a condition of the road surface in contact with the tire, a tire internal pressure state, and a tire abrasion state;

wherein the control device estimates that the condition of the road surface in contact with the tire has changed from an appropriate road surface to a low-friction road surface when the control device detects the first correlation strength having increased by the first threshold or more and the second correlation strength having decreased by the second threshold or more;

wherein the control device estimates that the tire internal pressure state has decreased when the control device detects the first correlation strength having decreased by the first threshold or more and the second correlation strength having decreased by the second threshold or more; and wherein the control device estimates the tire abrasion state has progressed when the control device detects the first correlation strength having decreased by the first threshold or more and the second correlation strength having increased by the second threshold or more.

6. The tire contact state estimation system according to claim 5, the control device detects whether a mean value of the first correlation strength for a predetermined period has increased or decreased by the first threshold or more with respect to the predetermined first reference value and also detects whether a mean value of the second correlation strength for the predetermined period has increased or decreased by the second threshold or more with respect to the predetermined second reference value, wherein the predetermined period associated with a result of the detection used to estimate the tire internal pressure state is longer than the predetermined period associated with a result of the detection used to estimate the condition of the road surface in contact with the tire.

7. The tire contact state estimation system according to claim 6, the control device detects whether a mean value of the first correlation strength for a predetermined period has increased or decreased by the first threshold or more with respect to the predetermined first reference value and also detects whether a mean value of the second correlation strength for the predetermined period has increased or decreased by the second threshold or more with respect to the predetermined second reference value, wherein
the predetermined period associated with a result of the detection used to estimate the tire abrasion state is longer than the predetermined period associated with a result of the detection used to estimate the condition of the road surface in contact with the tire and the tire internal pressure state.

8. The tire contact state estimation system according to claim 5, the control device detects whether a mean value of the first correlation strength for a predetermined period has increased or decreased by the first threshold or more with respect to the predetermined first reference value and also detects whether a mean value of the second correlation strength for the predetermined period has increased or decreased by the second threshold or more with respect to the predetermined second reference value, wherein
the predetermined period associated with a result of the detection used to estimate the tire abrasion state is longer than the predetermined period associated with a result of the detection used to estimate the condition of the road surface in contact with the tire and the tire internal pressure state.

9. A tire contact state estimation system of estimating information on a contact state of a tire mounted on a vehicle to a road surface, the tire contact state estimation system comprising:
a control device, a wheel speed detection device detecting a rotational velocity of the tire and outputting detection data to the control device, a wheel braking and driving force detection device detecting a braking and driving force of the tire and outputting detection data to the control device, a steering angle detection device detecting a slip angle of the tire and outputting detection data to the control device, a steering force detection device detecting a generated lateral force of the tire and outputting detection data to the control device, and a display device connected to the control device so that, when the control device detects an abnormal contact state of the tire to the road surface, the display device displays a warning,
wherein the control device calculates a first correlation strength between the rotational velocity and the braking and driving force from the information on the rotational velocity of the tire from the input of the wheel speed detection device and the information on the braking and driving force of the tire from the input of the wheel braking and driving force detection device;
wherein the control device calculates each of the first correlation strengths in seconds as a unit, in days or months as a unit, or in years as a unit;
wherein the control device calculates a second correlation strength between the slip angle and the generated lateral force from the information on the slip angle of the tire from the input of the steering angle detection device, and the information on the generated lateral force of the tire from the input of the steering force detection device;
wherein the control device calculates each of the second correlation strengths in seconds as a unit, in days or months as a unit, or in years as a unit;
wherein the control device includes information of a predetermined first reference value with respect to each of the first correlation strengths in seconds as a unit, in days or months as a unit, or in years as a unit;
wherein the control device includes information of a first threshold with respect to each of the predetermined first reference values in seconds as a unit, in days or months as a unit, or in years as a unit;
wherein the control device includes information of a predetermined second reference value with respect to each of the second correlation strengths in seconds as a unit, in days or months as a unit, or in years as a unit;
wherein the control device includes information of a second threshold with respect to each of the predetermined first reference values in seconds as a unit, in days or months as a unit, or in years as a unit;
wherein the control device estimates, based on a result of a detection at the control device, at least two of the following: a condition of the road surface in contact with the tire, a tire internal pressure state, and a tire abrasion state;
wherein the control device estimates that the condition of the road surface in contact with the tire has changed from an appropriate road surface to a low-friction road surface when the control device detects that the first correlation strength in seconds as a unit has increased by the first threshold in seconds as a unit or more, and the second correlation strength in seconds as a unit has decreased by the second threshold in seconds as a unit or more;
wherein the control device estimates that the tire internal pressure state has decreased when the control device detects that the first correlation strength in days or months as a unit has decreased by the first threshold in days or months as a unit or more, and the second correlation strength in days or months as a unit has decreased by the second threshold in days or months as a unit or more; and
wherein the control device estimates the tire abrasion state has progressed when the control device detects that the first correlation strength in years as a unit has increased by the first threshold in years as a unit or more, and the second correlation strength in years as a unit has increased by the second threshold in years as a unit or more.

10. The tire contact state estimation system according to claim 9, wherein the control device detects whether a mean value of the first correlation strength for a predetermined period has increased or decreased by the first threshold or more with respect to the predetermined first reference value and also detecting whether a mean value of the second correlation strength for the predetermined period has increased or decreased by the second threshold or more with respect to the predetermined second reference value, wherein
the predetermined period associated with a result of the detection used to estimate the tire internal pressure state is longer than the predetermined period associated with a result of the detection used to estimate the condition of the road surface in contact with the tire.

11. The tire contact state estimation system according to claim 10, wherein the control device detects whether a mean value of the first correlation strength for a predetermined period has increased or decreased by the first threshold or more with respect to the predetermined first reference value and also detecting whether a mean value of the second correlation strength for the predetermined period has increased or decreased by the second threshold or more with respect to the predetermined second reference value, wherein the predetermined period associated with a result of the detection at the change detection step used to estimate the tire abrasion state is longer than the predetermined period associated with a result of the detection used to estimate the condition of the road surface in contact with the tire and the tire internal pressure state.

12. The tire contact state estimation system according to claim 9, wherein the control device detects whether a mean value of the first correlation strength for a predetermined period has increased or decreased by the first threshold or more with respect to the predetermined first reference value and also detecting whether a mean value of the second correlation strength for the predetermined period has increased or decreased by the second threshold or more with respect to the predetermined second reference value, wherein the predetermined period associated with a result of the detection used to estimate the tire abrasion state at the estimation step is longer than the predetermined period associated with a result of the detection used to estimate the condition of the road surface in contact with the tire and the tire internal pressure state.

\* \* \* \* \*